United States Patent
Ishikawa et al.

(10) Patent No.: US 9,675,260 B2
(45) Date of Patent: Jun. 13, 2017

(54) PHOTOBIOLOGICAL MEASUREMENT APPARATUS

(71) Applicant: Shimadzu Corporation, Kyoto-shi (JP)

(72) Inventors: Akihiro Ishikawa, Kyoto (JP); Yoshihiro Inoue, Kyoto (JP); Takashi Amita, Kyoto (JP); Satoru Kohno, Kyoto (JP); Yoshinori Masuda, Kyoto (JP); Haruhide Udagawa, Kyoto (JP)

(73) Assignee: SHIMADZU CORPORATION, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 472 days.

(21) Appl. No.: 14/524,108

(22) Filed: Oct. 27, 2014

(65) Prior Publication Data

US 2015/0105672 A1    Apr. 16, 2015

Related U.S. Application Data

(63) Continuation of application No. PCT/JP2012/061059, filed on Apr. 25, 2012.

(51) Int. Cl.
  *A61B 6/00*      (2006.01)
  *A61B 5/026*     (2006.01)
  (Continued)

(52) U.S. Cl.
  CPC .......... *A61B 5/0261* (2013.01); *A61B 5/0042* (2013.01); *A61B 5/14552* (2013.01);
  (Continued)

(58) Field of Classification Search
  CPC ............. A61B 5/0261; A61B 5/14552; A61B 5/14553
  (Continued)

(56) References Cited

FOREIGN PATENT DOCUMENTS

JP    2008-064675    3/2008
JP    2009-095380    5/2009
(Continued)

OTHER PUBLICATIONS

International Search Report of PCT/JP2012/061059 mailed May 22, 2012.
(Continued)

*Primary Examiner* — Amanda Patton
*Assistant Examiner* — Philip C Edwards
(74) *Attorney, Agent, or Firm* — Muir Patent Law PLLC (57) ABSTRACT

A photobiological measurement apparatus 1 may include a second received light quantity information calculation unit 33 for calculating measurement data relating to cerebral activity, a data display controller for displaying the measurement data for a specified area of a subject's brain, is characterized: is being provided with a reference light-receiving probe 14, which is disposed at a position separated by a first setting distance r1 from the light-transmitting prober 12 that is shorter than a second setting distance r2, and a first received light quantity information calculating unit 32, which calculates skin blood flow data relating to the skin blood flow using first received light quantity information $\Delta A1$ from the light transmitting probe 12 to the reference light-receiving probe 14, and in displaying the skin blood flow data at a specified position of the subject's scalp by indicating the measurement position on the subject's scalp and displaying the skin blood data.

4 Claims, 9 Drawing Sheets

(51) Int. Cl.
    *A61B 5/1455*    (2006.01)
    *A61B 5/00*    (2006.01)
(52) U.S. Cl.
    CPC ........ *A61B 5/14553* (2013.01); *A61B 5/6814* (2013.01); *A61B 2562/046* (2013.01)
(58) Field of Classification Search
    USPC ........................................................ 600/479
    See application file for complete search history.

(56)    References Cited

FOREIGN PATENT DOCUMENTS

| JP | 2009-136434 | 6/2009 |
| JP | 2009-172177 | 8/2009 |
| JP | 2010-119660 | 6/2010 |

OTHER PUBLICATIONS

"Direct characterization and removal of interfering absorption trends in two-layer turbid media," J. Opt. Soc. Am. A/vol. 22, No. 9, Sep. 2005, pp. 1874-1882.

"Optical measurements of absorption changes in two-layered diffusive media," Phys. Med. Biol. 49 (2004), pp. 1183-1201.

Measured data

Skin blood flow data

PHOTOBIOLOGICAL MEASUREMENT APPARATUS

RELATED APPLICATIONS

This is a continuation of International Application PCT/JP2012/061059, with an international filing date of Apr. 25, 2012, the contents of which are incorporated by reference in their entirety.

TECHNICAL FIELD

The present invention relates to a photobiological measurement apparatus, and more specifically to a photobiological measurement apparatus for measuring cerebral activity in a noninvasive manner.

BACKGROUND TECHNOLOGY

In recent years, for the purpose of observing cerebral activity status, an optical cerebral function imaging apparatus capable of conveniently measuring cerebral activity status using lights in a noninvasive manner has been developed. In such an optical cerebral function imaging apparatus, a light-transmitting probe arranged on a scalp surface of a subject irradiates near-infrared light of three different types of wavelengths $\lambda_1, \lambda_2, \lambda_3$ (e.g., 780 nm, 805 nm, 830 nm) on to a brain. While, a light-receiving probe arranged on the scalp surface detects an intensity change (received light quantity information) $\Delta A(\lambda_1), \Delta A(\lambda_2), \Delta A(\lambda_3)$ of each of the near-infrared lights of wavelengths $\lambda_1, \lambda_2, \lambda_3$ reflected from the brain.

In order to obtain the product of the change in oxyhemoglobin concentration and the optical path length [oxyHb] in a cerebral blood flow and the product of the change in deoxyhemoglobin and the optical path length [deoxyHb] from received light quantity information $\Delta A(\lambda_1), \Delta A(\lambda_2), \Delta A(\lambda_3)$ obtained as mentioned above, equations (1), (2) and (3) using a Modified Beer Lambert law may be solved. Further, from the product of the change in oxyhemoglobin concentration and the optical path length [oxyHb] and the product of the change in deoxyhemoglobin and the optical path length [deoxyHb], a product of the change in total hemoglobin and the optical path length ([oxyHb]+[deoxyHb]) is calculated.

$$\Delta A(\lambda_1) = E_O(\lambda_1) \times [\text{oxyHb}] + E_d(\lambda_1) \times [\text{deoxyHb}] \quad (1)$$

$$\Delta A(\lambda_2) = E_O(\lambda_2) \times [\text{oxyHb}] + E_d(\lambda_2) \times [\text{deoxyHb}] \quad (2)$$

$$\Delta A(\lambda_3) = E_O(\lambda_3) \times [\text{oxyHb}] + E_d(\lambda_3) \times [\text{deoxyHb}] \quad (3)$$

$E_O(\lambda_m)$ denotes an absorbance coefficient of oxyhemoglobin in the light having a wavelength $\lambda m$, and $E_d(\lambda_m)$ denotes an absorbance coefficient of deoxyhemoglobin in the light having a wavelength $\lambda_m$.

Figure 7A:
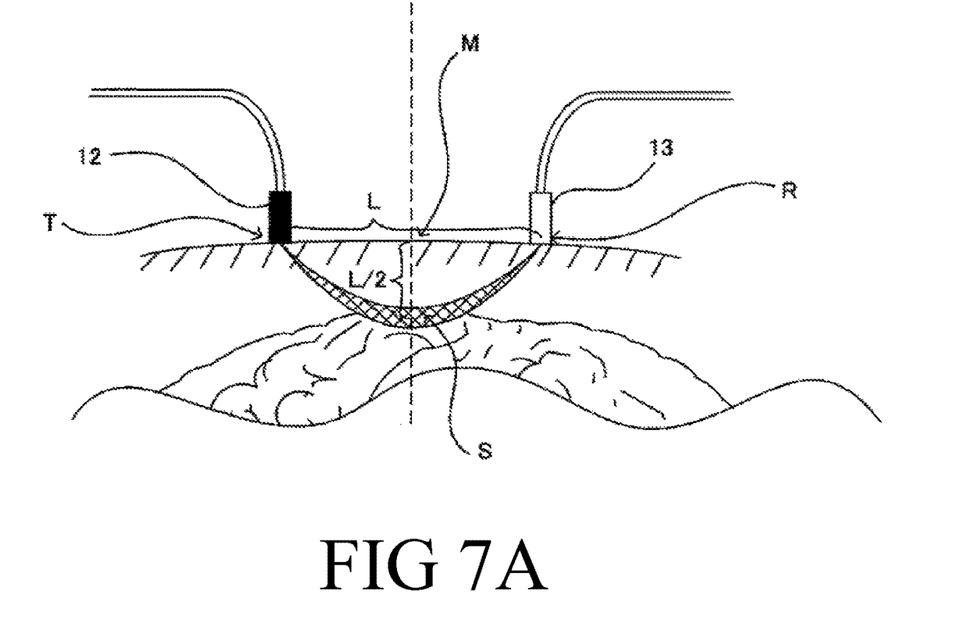
FIGS. 7A and 7B show a relation between a pair of light-transmitting probe and light-receiving probe and a measurement position.
Figure 7B:
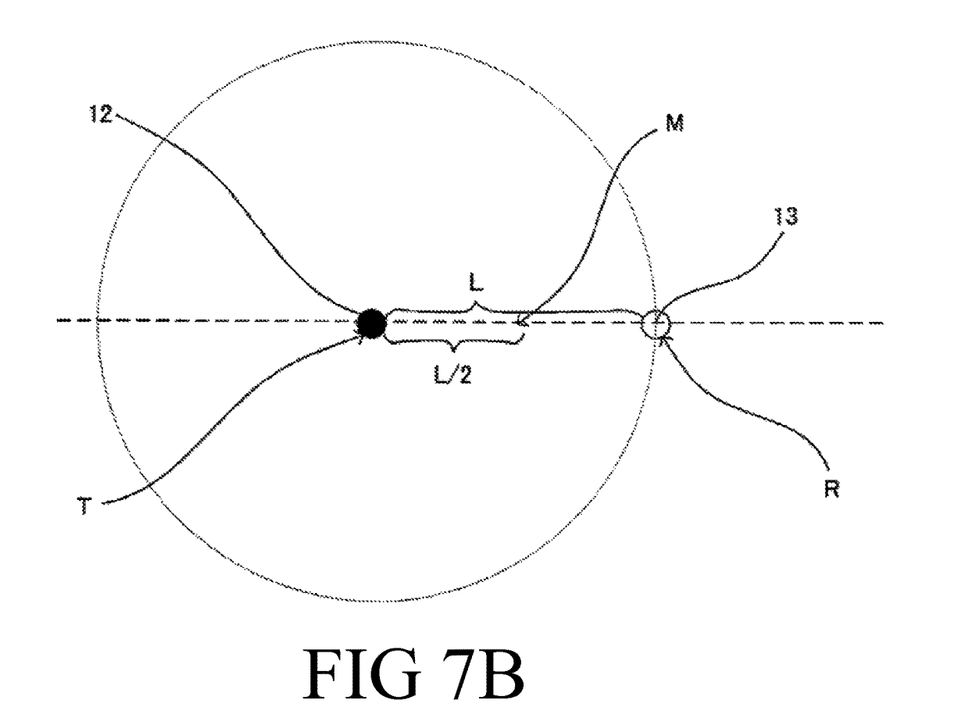

Here, the relation between a distance (channel) between a light-transmitting probe and a light-receiving probe and a measurement position will be explained. FIGS. 7A and 7B show a relation between a pair of light-transmitting probe and light-receiving probe and a measurement position. A light-transmitting probe 12 is pressed into contact with a light-transmitting point T on a scalp surface of a subject, while a light-receiving probe 13 is pressed into contact with a light-receiving point R on the scalp surface of the subject. The light-transmitting probe 12 irradiates lights, and the light-receiving probe 13 receives lights reflected back to the scalp surface. At this time, lights passed through a banana-shaped region (measurement region) among lights irradiated from the light-transmitting point T on the scalp surface reach the light-receiving point R on the scalp surface. That is, the lights pass through blood vessels existing in the skin close to the light-transmitting point T, blood vessels existing in the brain, and blood vessels existing in the skin close to the light-receiving point R.

Figure 8:
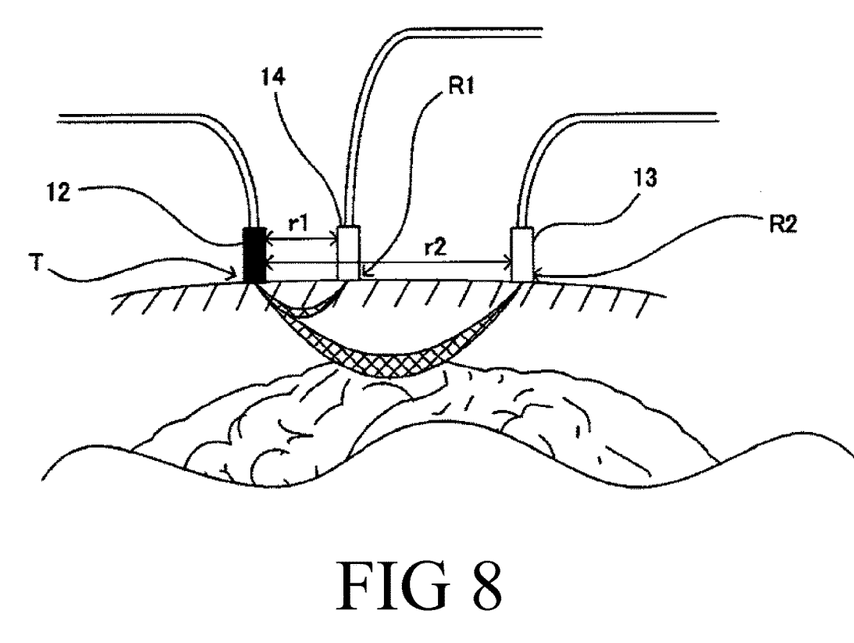
FIG. 8 is a plan view showing a relation between the reference light-receiving probe away from the light-transmitting probe by a short distance r1 and the light-receiving probe away from the light-transmitting probe by a long distance r2 and a measurement position.

Under the circumstances, in order to obtain received light information $\Delta A$ relating only to blood vessels existing in the brain, a distance (channel) between the light-transmitting probe 12 and the light-receiving probe 13 is set to a short distance r1 and a distance (channel) between the light-transmitting probe 12 and the light-receiving probe 13 is set to a long distance r2 (see, e.g., Patent Document 1 or non-Patent Document 1). FIG. 8 is a cross-sectional view showing a relation between a reference light-receiving probe 14 arranged at a short distance r1 away from the light-transmitting probe 12, a light-receiving probe 13 arranged at a long distance r2 away from the light-transmitting probe 12 and measurement positions. With this, from the channel having the long distance r2, light quantity information $\Delta A2$ is received. Light quantity information $\Delta A2$ relates to blood vessels existing in the skin close to the light-transmitting point T, blood vessels existing in the brain, and blood vessels existing in the skin close to the light-receiving point R2. From the channel having the short distance r1, light quantity information $\Delta A1$ relating only to blood vessels existing in the skin close to the light-transmitting point T (blood vessels existing in the skin close to the light-receiving point R1) is received.

From the received light quantity information $\Delta A1$ and $\Delta A2$ obtained as mentioned above, using the following Equation (4), received light quantity information $\Delta A$ relating only to blood vessels existing in the brain is obtained.

$$\Delta A = \Delta A2 - K\Delta A1 \quad \text{Equation (4)}$$

In Equation (4), in order to obtain the received light quantity information $\Delta A$, it is necessary to specify the coefficient(s) K. See, for example, Non-Patent Document 2 for a method for calculating the coefficient(s) K is disclosed. In this calculation method, the coefficient(s) K is calculated using a least square error.

Further, in an optical cerebral function imaging device, it is performed to respectively measure a product of the density change of oxyhemoglobin and the optical path length [oxyHb], a product of the density change of deoxyhemoglobin and the optical length [deoxyHb], and a product of the density change of total hemoglobin and the optical length ([oxyHb]+[deoxyHb]), which relate to a plurality of measuring points of the brain.

Figure 9:
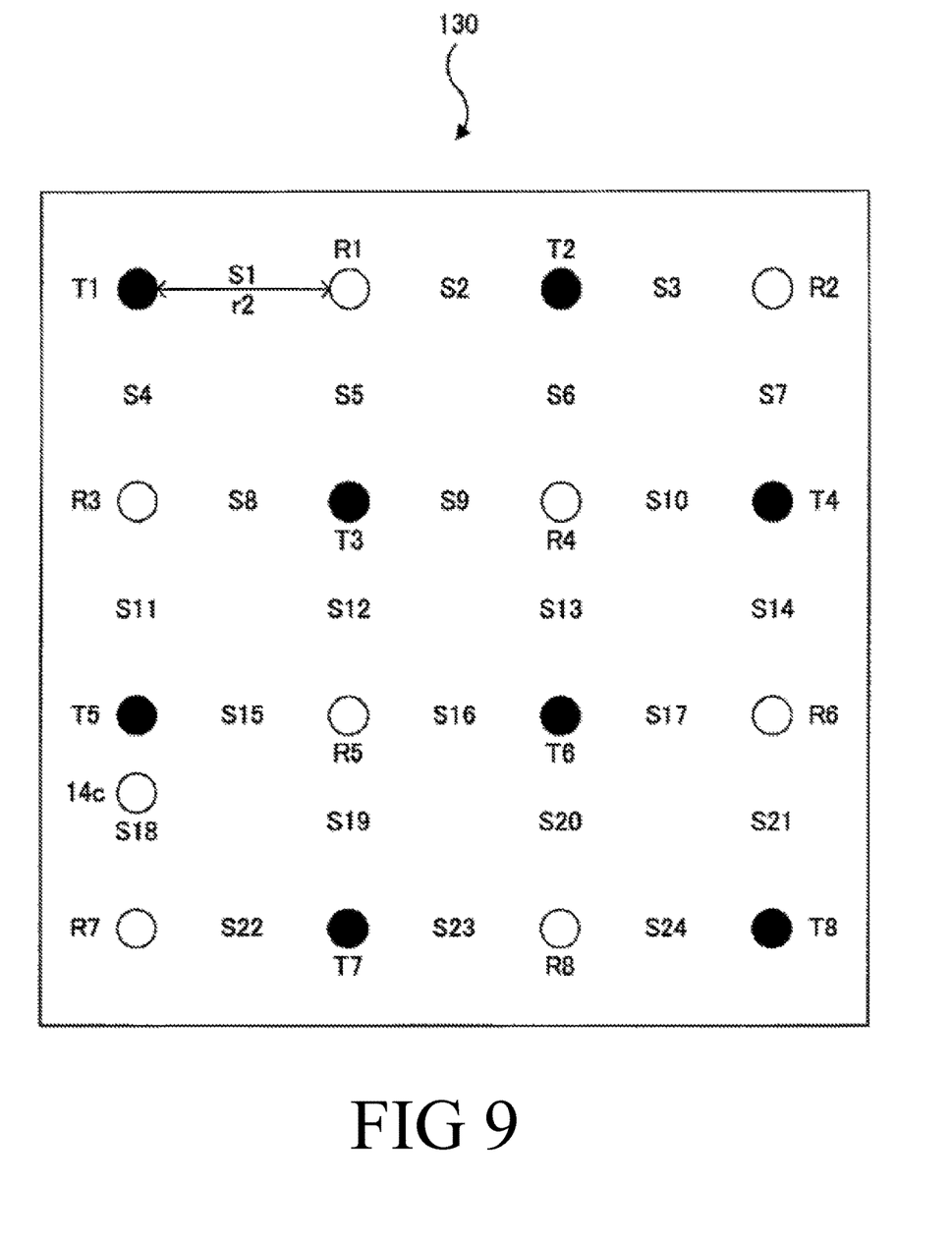
FIG. 9 is a plan view showing one example of a holder into which eight (8) light-transmitting probes and eight (8) light-receiving probes are inserted.

In such an optical cerebral function imaging device, in order to bring eight (8) light-transmitting probes 12 and eight (8) light-receiving probes 13 into contact with a scalp surface of a subject in a predetermined arrangement, a holder (light-transmitting/receiving unit) 130 is used. FIG. 9 is a plan view showing one example of the holder 130 into which eight (8) light-transmitting probes and eight (8) light-receiving probes are inserted.

The light-transmitting probes $12_{T1}$ to $12_{T8}$ and light-receiving probes $13_{R1}$ to $13_{R8}$ are arranged alternately such that four (4) probes are arranged in the lengthwise direction and four (4) probes are arranged in the lateral direction. In this arrangement, the second setting distance r2 which is a distance (channel) between the light-transmitting probe $12_{T1}$ to $12_{T8}$ and the light-receiving probe $13_{R1}$ to $13_{R8}$ is set to 30 mm. With this, received light quantity information $\Delta A_2(\lambda_1)$, $\Delta A_2(\lambda_2)$, and $\Delta A_2(\lambda_3)$) relating to twenty-four (24) measurement positions on a brain are obtained.

RELATED ART

Patent Document

PATENT DOCUMENT 1: Japanese Unexamined Patent Application Publication No. 2009-136434

Non-Patented Document

NON-PATENT DOCUMENT 1: Rolf B. Saager, and Andrew J. Berger "Direct characterization and removal of interfering absorption trends in two-layer turbid media" J. Opt. Soc. Am. A/Vol. 22, No. 9/September 2005.
NON-PATENT DOCUMENT 2: Francesco Fabbri, Angelo Sassaroli, Michael e Henry, and Sergio Fantini "Optical measurements of absorption of changes in two-layered diffusive media" Phys. Med. Biol. 49 (2004) 1183-1201.

SUMMARY

Received light quantity information $\Delta A$ may be calculated by the calculation method using received light information $\Delta A1$ and $\Delta A2$ and coefficient K as mentioned above. This considers a combination of a pair of light-transmitting probe 12 and light-receiving probe 13, but may not consider all combinations of a plurality of light-transmitting probes $12_{T1}$ to $12_{T8}$ and a plurality of light-receiving probes $13_{R1}$ to $13_{R8}$ mounted on the holder 130 of the aforementioned optical cerebral function imaging device. In other words, it was not configured to calculate the received light quantity information $\Delta A$ relating to the plural measurement positions (24 positions) on the brain.

In order to calculate the received light quantity information $\Delta A$ by the calculation method as mentioned above, a plurality of reference light-receiving probes 14 may be provided so that a short distance r2 is secured with respect to all combinations of light-transmitting probes $12_{T1}$ to $12_{T8}$ and light-receiving probes $12_{R1}$ to $12_{R8}$. In some instances, however, it may be considered costly to provide reference light-receiving probes 14 with respect to all combinations of light-transmitting probes $12_{T1}$ to $12_{T8}$ and light-receiving probes $13_{R1}$ to $13_{R8}$.

In some embodiments, a method is provided capable of considering received light quantity information $\Delta A$ relating only to blood vessels existing in the brain in a plurality of measurement positions of the brain even with a smaller number of reference light-receiving probes. The measurement data may be displayed in a predetermined range of a brain of a subject and also simultaneously display skin blood flow data at a predetermined position of a scalp of the subject. With this, doctors, laboratory technicians, etc., may consider the measurement data with reference to the skin blood flow data.

A photobiological measurement apparatus according to some embodiments includes a light-transmitting/receiving unit having a plurality of light-transmitting probes to be arranged on a scalp surface of a subject and a plurality of light-receiving probes to be arranged on the scalp surface, each of the light-receiving probes being arranged at a position away from the light-transmitting probe by a second setting distance r2, a second received light quantity information calculation unit configured to calculate measurement data relating to cerebral activity using second received light quantity information $\Delta A2$ from the light-transmitting probe to the light-receiving probe, a data display controller configured to display measurement data in a predetermined range of a brain of the subject by respectively displaying the measurement data by indicating measurement positions of the brain of the subject, a reference light-receiving probe arranged at a position away from the light-transmitting probe by a first setting distance r1 shorter than the second setting distance r2, and a first received light quantity information calculation unit configured to calculate skin blood flow data relating to a skin blood flow using first received light quantity information $\Delta A1$ from the light-transmitting probe to the reference light-receiving probe, wherein the data display controller displays the measurement data in the predetermined range of the brain of the subject and the skin blood flow data while showing measurement positions of the scalp of the subject to display skin blood flow data at the predetermined position of the scalp of the subject.

In this disclosure, the "second setting distance r2" denotes a distance for obtaining received light quantity information relating to blood vessels existing in a skin near the light-transmitting point T, blood vessels existing in the brain, and blood vessels existing in the akin near the light-receiving point R. The "first setting distance r1" denotes a distance for obtaining received light quantity information relating to blood vessels existing in a skin near the light-transmitting point T or the light-receiving point R.

Further, the "predetermined range of the brain of the subject" denotes an arbitral brain range desired to be measured, and may be decided by the size, etc., of the light-transmitting/receiving unit. The "predetermined position of the scalp of the subject" denotes a position for measuring blood vessels not existing in the brain, which can be exemplified, for example, a position, etc., for measuring main arteries or veins existing within 1.5 cm from the scalp, arteries near the light-transmitting/receiving unit, or veins near the light-transmitting/receiving unit.

According to some embodiments, a photobiological measurement apparatus may provide doctors, laboratory technicians, etc., measurement data considering the skin blood flow data and the corresponding measurement positions, and therefore it may be possible to judge whether artifacts are generated in the measurement data or what artifacts are generated in which measurement data. As a result, doctors, laboratory technicians, etc., can discard certain measurement data, enabling accurate diagnosis of the cerebral activity of the subject.

Further, in the photobiological measurement apparatus according to some embodiments, the data display controller may be configured to display the measurement data in the predetermined range of the brain of the subject with a map, and also to display the skin blood flow data at a position near the predetermined position of the scalp of the subject in the map. The map may be a map in which positions are correlated to a two-dimensional or three-dimensional space.

Further, in the photobiological measurement apparatus according to some embodiments, the apparatus may include a plurality of reference light-receiving probes, wherein the data display controller may be configured to display the measured data in the predetermined range of the brain of the subject with a map, and also to display the skin blood flow data in the predetermined rang of the scalp of the object.

Further, in the photobiological measurement apparatus according to some embodiments, the apparatus may include a morphological image display controller configured to obtain and display a scalp surface morphological image showing a scalp surface of the subject and/or a brain surface morphological image showing a brain surface of the subject, wherein the map may be displayed on a scalp surface morphological image and/or the brain surface morphological image in a superimposed manner.

The scalp surface morphological image showing the scalp surface of the subject may denote a three-dimensional morphological image created by extracting visual data showing a scalp surface from visual data of the subject created by a nuclear magnetic resonance image diagnostic device (hereinafter abbreviated as MRI), a CT image, etc. Further, the brain surface morphological image showing the brain surface of the subject may be a three-dimensional morphological image created by extracting visual data showing a brain surface from visual data of the subject created by an MRI, a CT image, etc.

A three-dimensional morphological image showing a scalp surface and a brain surface may be created, and therefore, regardless of individual difference of the cerebral anatomical structure, the cerebral activity can be considered in detail.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

In the drawings, the size and relative sizes of layers and regions may be exaggerated for clarity. Like numbers refer to like elements throughout. The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/". It will be understood that, although the terms first, second, etc. may be used herein to describe various elements, these elements should not be limited by these terms. Unless indicated otherwise, these terms are only used to distinguish one element from another. For example, a first object could be termed a second object, and, similarly, a second object could be termed a first object without departing from the teachings of the disclosure.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present.

Other words used to describe the relationship between elements should be interpreted in a like fashion (e.g., "between" versus "directly between," "adjacent" versus "directly adjacent," etc.). However, the term "contact," as used herein refers to direct contact (i.e., touching) unless the context indicates otherwise.

Terms such as "same," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

DETAILED DESCRIPTION

Hereinafter, embodiments of the present invention will be explained with reference to drawings. It should be noted that the present invention is not limited to the embodiments explained below, and covers various embodiments within a range not deviating from the spirit of the present invention.

Figure 1:
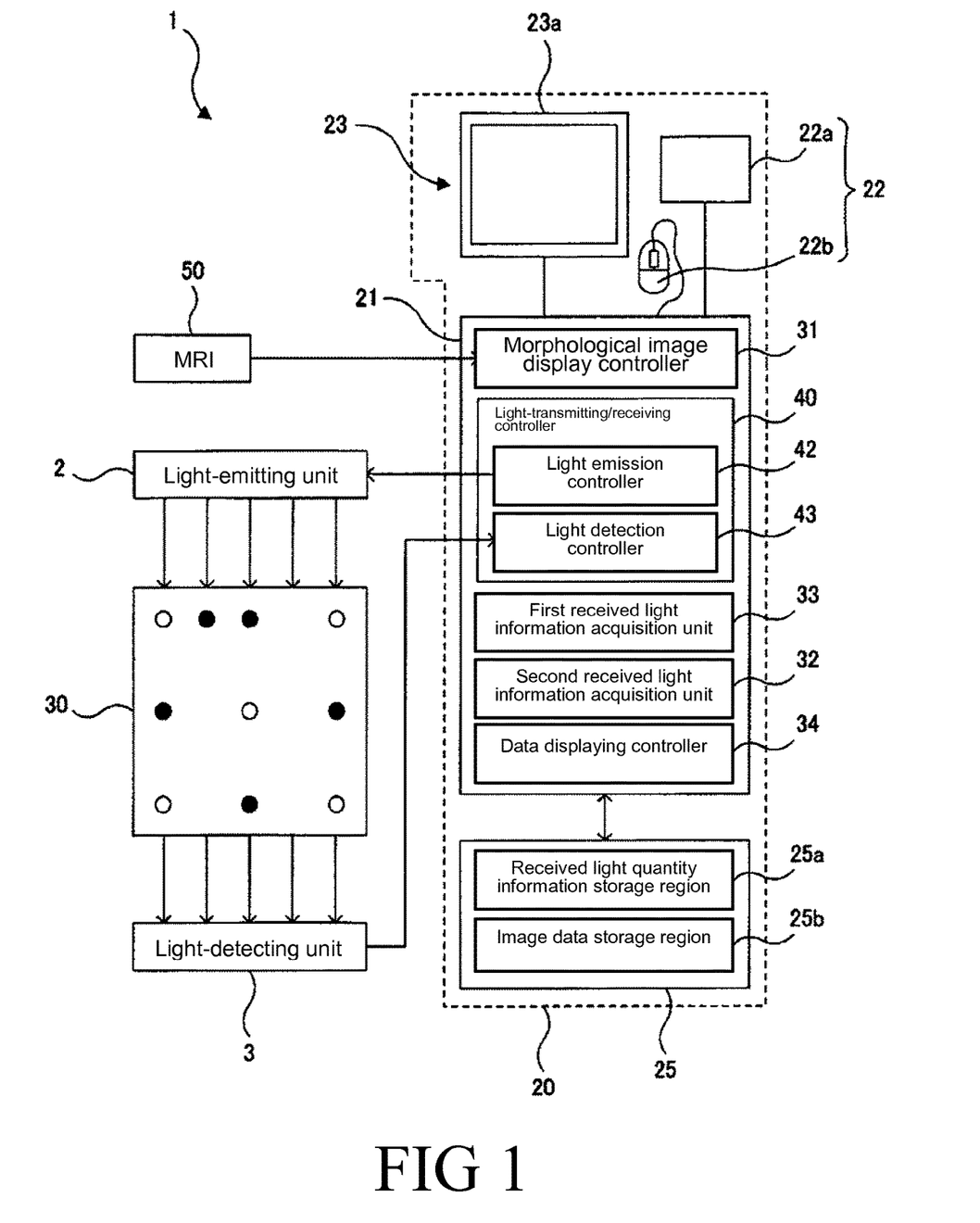
FIG. 1 is a block diagram showing a structure of a photobiological measurement apparatus according to one embodiment of the present invention.
Figure 2:
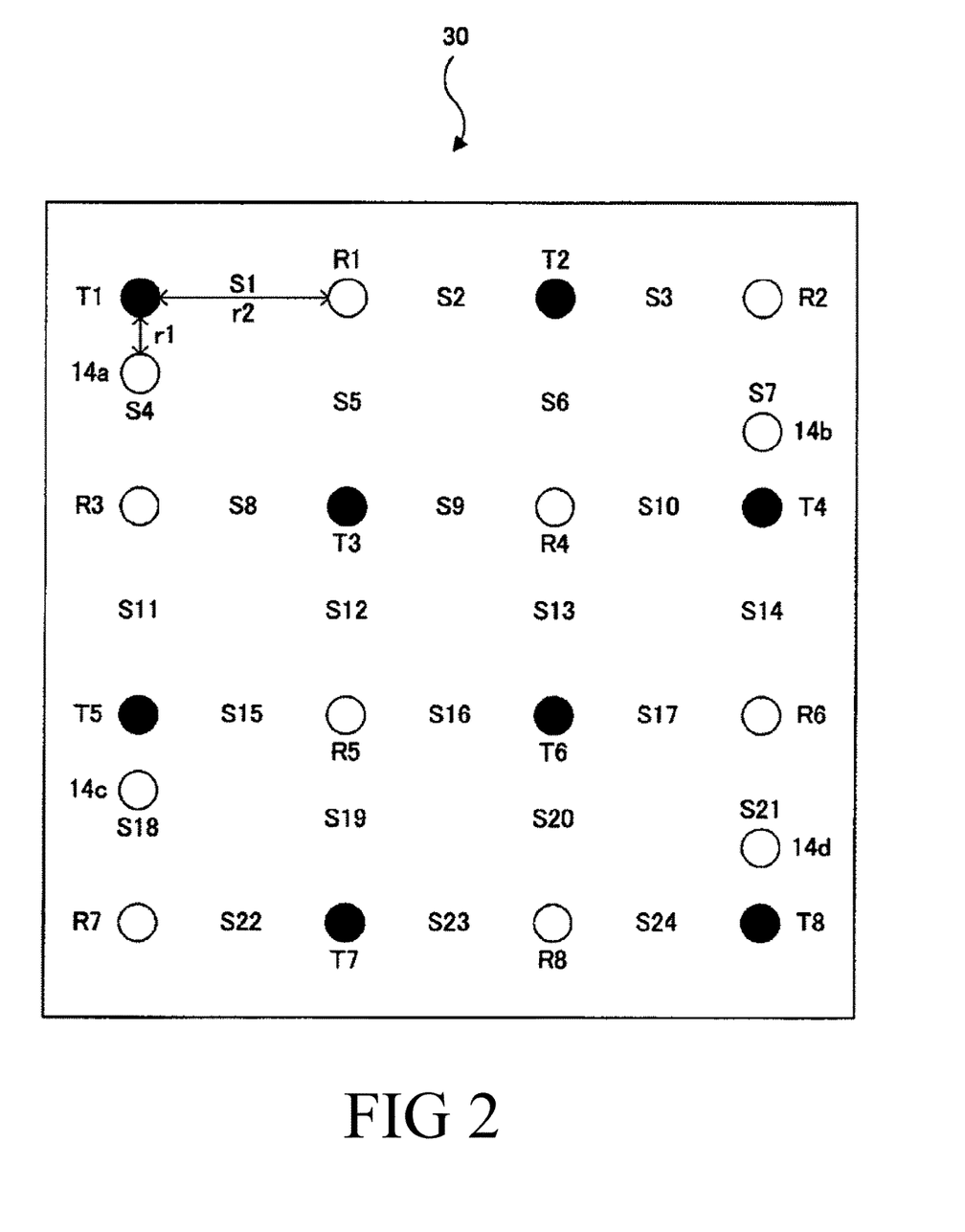
FIG. 2 is a plan view showing an example of a holder into which eight light-transmitting probes, eight light-receiving probes, and four reference light-receiving probes are inserted.
Figure 3:
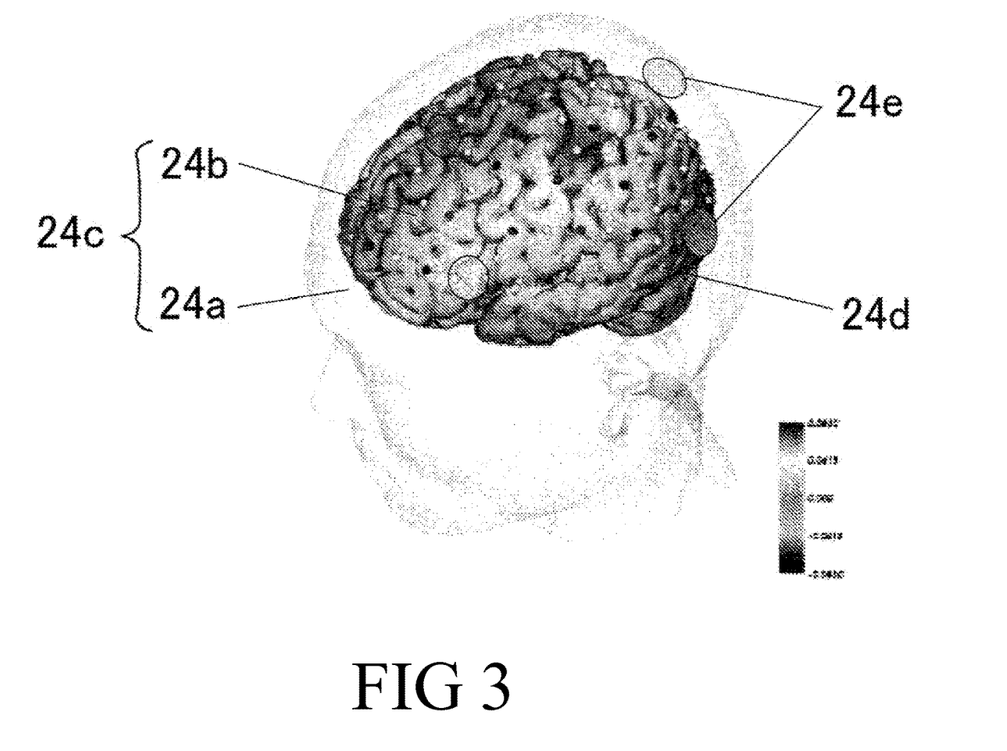
FIG. 3 is a view showing an example of a monitor screen displaying an image obtained by the photobiological measurement apparatus.

FIG. 1 is a block diagram showing a structure of a photobiological measurement apparatus according to one embodiment of the present invention. Further, FIG. 2 is a plan view showing one example of a holder (light-transmitting/receiving unit) into which eight (8) light-transmitting probes, eight (8) light-receiving probes, and four (4) reference light-receiving probes are inserted. FIG. 3 is a view showing one example of a monitor screen displaying an image as a measurement result.

The photobiological measurement apparatus 1 is constituted by a holder 30, a light-emitting unit 2, a light-detecting unit 3, and a controller (computer) 20 which executes entire control of the photobiological measurement apparatus 1.

In FIG. 3, a three-dimensional morphological image 24c showing the positional relation between a scalp surface image 24a and a brain surface image 24b is displayed. Further, on predetermined twenty-four (24) positions on the brain surface image 24b, the measurement data 24d is imaged, and on four (4) positions on the scalp surface image 24a, the skin blood flow data 24e is imaged. Each of the twenty-four (24) positions may correspond to an area between one of the light-transmitting probes $12_{T1}$ to $12_{T8}$ irradiate lights a neighboring one of the light-receiving probes $13_{R1}$ to $13_{R8}$. For example, receiving probe $13_{R1}$ may be used to image a first area of the brain surface between receiving probe $13_{R1}$ and light-transmitting probes $12_{T1}$, a second area of the brain surface between receiving probe $13_{R1}$ and light-transmitting probes $12_{T2}$ and a third area of the brain surface between receiving probe $13_{R1}$ and light-transmitting probes $12_{T3}$. The measurement data 24d and the skin blood flow data 24e are shown by colors corresponding to the numerical values of the product of the change in oxyhemoglobin concentration and the optical path length [oxyHb] at a certain measurement time t. Further, the scalp surface image 24a and the skin blood flow data are imaged translucently.

The holder 30 is provided with eight (8) light-transmitting probes $12_{T1}$ to $12_{T8}$, eight (8) light-receiving probes $13_{R1}$ to $13_{R8}$, and four (4) reference light-receiving probes 14a to 14d. The light-transmitting probes $12_{T1}$ to $12_{T8}$ irradiate lights, while the light-receiving probes $13_{R1}$ to $13_{R8}$ and the reference light-receiving probes 14a to 14d detect an amount of light.

The light-transmitting probes $12_{T1}$ to $12_{T8}$ and the light-receiving probes $13_{R1}$ to $13_{R8}$ are arranged alternately in the line direction and in the row direction in a square lattice-like manner. At this time, the second setting distance r2 which is an interval (channel) between the light-transmitting probe $12_{T1}$ to $12_{T8}$ and the light-receiving probe $13_{R1}$ to $13_{R8}$ is set to 30 mm.

Further, the reference light-receiving probe 14a is arranged at a position between the light-transmitting probe $12_{T1}$ and the light-receiving probe $13_{R3}$ and away from the light-transmitting probe $12_{T1}$ by a first setting distance r1. The first setting distance r1 which is an interval between the light-transmitting probe $12_{T1}$ and the reference light-receiving probe 14a is set to 10 mm. Then, the light-receiving probe 14b is arranged at a position between the light-transmitting probe $12_{T4}$ and the light-receiving probe $13_{R2}$ and away from the light-transmitting probe $12_{T4}$ by the first setting distance r1. The light-receiving probe 14c is arranged at a position between the light-transmitting probe $12_{T5}$ and the light-receiving probe $13_{R7}$ and away from the light-transmitting probe $12_{T5}$ by the first setting distance r1. The light-receiving probe 14d is arranged at a position between the light-transmitting probe $12_{T8}$ and the light-receiving probe $13_{R6}$ and away from the light-transmitting probe $12_{T8}$ by the first setting distance r1.

The light-emitting unit 2 emits light to a single light-transmitting probe 12 selected from eight (8) light-transmitting probes $12_{T1}$ to $12_{T8}$ in accordance with a driving signal input from the computer 20. As the aforementioned light, near-infrared light (e.g., three wavelength lights of 780 nm, 805 nm, and 830 nm) is used.

The light-detecting unit 3 separately detects near-infrared lights (e.g., three wavelength lights of 780 nm, 805 nm, and 830 nm) received by the eight (8) light-receiving probes $13_{R1}$ to $13_{R8}$ and outputs eight (8) first received light quantity information $\Delta A2_y(\lambda_1)$, $\Delta A2_y(\lambda_2)$ and $\Delta A2_y(\lambda_3)$ (y=1, 2, . . . 8) to the computer 20. Further, the light-detecting unit 3 separately detects near-infrared lights (e.g., three wavelength lights of 780 nm, 805 nm, and 830 nm) received by the four (4) reference light-receiving probes 14a to 14d and outputs four (4) first received light quantity information $\Delta A1_m(\lambda_1)$, $\Delta A1_m(\lambda_2)$ and $\Delta A1_m(\lambda_3)$ (y=1, 2, . . . 4) to the computer 20.

In the computer 20, a CPU 21 and a memory 25 are provided, and a display unit 23 having a monitor screen 23a, etc., and an input device 22 having a keyboard 22a, a mouse 22b, etc., are connected to the CPU and the memory. Explaining the functions to be processed by the CPU 21 in a blocked manner, the CPU 21 includes a light-transmitting/receiving controller 40, a morphological image display controller 31, and a second received light quantity information acquisition unit 32, and a first received light quantity information acquisition unit 33, and a data display controller 34. Further, in the memory 25, a received light quantity information storage region 25a for sequentially storing the received light quantity information $\Delta A1_m(\lambda_1)$, $\Delta A1_m(\lambda_2)$, $\Delta A1_m(\lambda_3)$, $\Delta A2_y(\lambda_1)$, $\Delta A2_y(\lambda_2)$, and $\Delta A2_y(\lambda_3)$, and an image data storage region 25b for storing image data are formed.

The morphological image display controller 31 acquires visual data created by an MRI 50 before measurement, obtains scalp surface morphological image data by extracting the visual data showing a scalp surface and also obtains brain surface morphological image data by extracting the visual data showing a brain surface, and stores the scalp surface morphological image data and the brain surface morphological image data to the image data storage region 25b. Here, the MRI 50 is configured to create visual data showing two-dimensional images in three directions. The visual data shows a subject including the scalp surface and the brain surface. Further, the visual data is constituted by a plurality of pixels having numerical values such as intensity information or phase information of an MR signal. As the aforementioned extracting methods, for example, an image region dividing method, such as, e.g., a region expansion method, a region merger method, or Heuristic law, using a plurality of pixels having numerical values such as intensity information or phase information of an MR signal, a method for extracting areas by connecting boundary elements, a method for extracting areas by deforming closed curves, can be exemplified.

The morphological image display controller 31 controls such that a three-dimensional morphological image 24d showing the positional relation between the scalp surface image 24a and the brain surface image 24b is created by synthesizing the scalp surface morphological image data and the brain surface morphological image data stored in the image data storage based on the input signal output from the input device after the measurement, etc., and the three-dimensional morphological image 24c is displayed on the monitor screen 23a (see FIG. 3).

The light-transmitting/receiving section controller 40 includes a light emission controller 42 which outputs a driving signal to the light-emitting unit 2 and a light detection controller 43 which makes the received light quantity information storage region 25a store received light quantity information $\Delta A1_m(\lambda_1)$, $\Delta A1_m(\lambda_2)$, $\Delta A1_m(\lambda_3)$, $\Delta A2_y(\lambda_1)$, $\Delta A2_y(\lambda_2)$, $\Delta A2_y(\lambda_3)$ upon receipt thereof from the light-detecting unit 3. The light emission controller 42 performs control of outputting a driving signal for transmitting light to the light-transmitting probe 12. The light detection controller 43 performs control of storing four (4) first received light quantity information $\Delta A1_m(\lambda_1)$, $\Delta A1_m(\lambda_2)$, and $\Delta A1_m(\lambda_3)$ obtained from the light-detecting unit 3 and eight (8) second received light quantity information $\Delta A2_y(\lambda_1)$, $\Delta A2_y(\lambda_2)$, and $\Delta A2_y(\lambda_3)$ obtained from the light-detecting unit 3 to the received light quantity information storage region 25a. In detail, every time light is transmitted from a single light-transmitting probe 12, four (4) first received light quantity information $\Delta A1_m(\lambda_1)$, $\Delta A1_m(\lambda_2)$, and $\Delta A1_m(\lambda_3)$ and eight (8) second received light quantity information $\Delta A2_y(\lambda_1)$, $\Delta A2_y(\lambda_2)$, and $\Delta A2_m(\lambda_3)$ are stored in the received light quantity information storage region 25a.

The second received light quantity information acquisition unit 32 performs control of acquiring the second received light quantity information $\Delta A2_x(\lambda_1)$, $\Delta A2_x(\lambda_2)$, and $\Delta A2_x(\lambda_3)$ (channel number x=1, 2, . . . , 24) detected by the light-receiving probe 13 apart from the light-transmitting probe 12 by a second setting distance r2, among the second received light quantity information $\Delta A2_y(\lambda_1)$, $\Delta A2_y(\lambda_2)$, and $\Delta A2_y(\lambda_3)$ stored in the received light quantity information storage region 25a. In other words, twenty-four second received light quantity information $\Delta A2_x(\lambda_1)$, $\Delta A2_x(\lambda_2)$, and $\Delta A2_x(\lambda_3)$ (x=1, 2, . . . 24) are acquired.

The first received light quantity information acquisition unit 33 performs control of acquiring the first received light quantity information $\Delta A1_n(\lambda_1)$, $\Delta A1_n(\lambda_2)$, and $\Delta A1_n(\lambda_3)$ (channel number n=1, 2, . . . , 4) detected by the reference light-receiving probe 14 apart from the light-transmitting probe 12 by a first setting distance r1, among the first received light quantity information $\Delta A1_m(\lambda_1)$, $\Delta A1_m(\lambda_2)$, and $\Delta A1_m(\lambda_3)$ stored in the received light quantity information storage region 25a. In other words, four (4) first received light quantity information $\Delta A1_n(\lambda_1)$, $\Delta A1_n(\lambda_2)$, and $\Delta A1_n(\lambda_3)$ (x=1, 2, . . . 4) are acquired.

The data display controller 34 performs control of displaying images of measurement data 24d on twenty-four (24) predetermined positions (or areas) of the brain surface image 24b by obtaining a product of the change in oxyhemoglobin concentration and the optical path length [oxyHb] and a product of the change in total hemoglobin concentration change and the optical path length ([oxyHb]+[deoxyHb]) as measurement data using the relational expression (1), (2) and (3), based on the second received light quantity information $\Delta A2_x(\lambda_1)$, $\Delta A2_x(\lambda_2)$, $\Delta A2_x(\lambda_3)$ (x=1, 2, . . . , 24) stored in the received light quantity information storage region 25a. The twenty-four (24) predetermined positions may respectively correspond to surface areas of the brain between a receiving probe $13_{Rn}$ and light-transmitting probes $12_{Tn}$. At this time, for example, products of the change in oxyhemoglobin concentration and the optical path length [oxyHb] at twenty-four (24) predetermined positions at a certain measurement time t is shown by colors based on a color table showing the correspondence relation between numeral values and colors. Further, each of twenty-four (24) predetermined positions of the brain surface image 24b may be a site S of the subject positioned at a depth corresponding to a half of a distance of a line connecting the light-transmitting point T and the light-receiving point R along the scalp surface of the subject by the shortest distance from the midpoint M of the line connecting the transmitting point T and the light-receiving point R along the scalp surface of the subject by the shortest distance.

Further, the data display controller 34 performs control of displaying images of measurement data 24d on twenty-four (24) predetermined positions of the brain surface image 24b and also displaying images of the skin blood flow data 24e on four (4) predetermined positions of the scalp surface image 24a by obtaining the product of the change in oxyhemoglobin concentration and the optical path length [oxyHb], the product of the change in deoxyhemoglobin concentration and the optical path length [deoxyHb], and the product of the change in total deoxyhemoglobin concentration and the optical path length ([oxyHb]+[deoxyHb]) as scalp blood flow data using the relational expressions (1), (2), and (3), based on the first received light quantity information $\Delta A1_n(\lambda_1)$, $\Delta A1_n(\lambda_2)$, $\Delta A1_n(\lambda_3)$ (n=1, 2, . . . , 4) stored in the received light quantity information storage region 25a. At this time, for example, products of the change in oxyhemoglobin concentration and the optical path length [oxyHb] at four (4) predetermined positions at a certain measurement time t is shown by colors based on a color table showing the correspondence relation between numeral values and colors. Each of the four (4) predetermined positions may correspond to an area or location of the scalp located between one of the four light-receiving probes 14a-14d and a neighboring the light transmitting probe $12_{Tn}$ (e.g., the nearest light transmitting probe $12_{Tn}$ or one spaced by the first setting distance r1). Each of four (4) predetermined positions of the scalp surface image 24a may be a mid-point M of a line connecting the light-transmitting point T and the light-receiving point R along the scalp surface of the subject by the shortest distance. With this, an image as shown in FIG. 3 is displayed on the monitor screen 23a.

As explained above, according to the photobiological measurement apparatus 1, doctors, laboratory technicians, etc., can consider the measurement data 24d considering the scalp blood flow data 24e and the measurement positions using the image as shown in FIG. 3. Therefore, it becomes possible to judge whether artifacts are generated in the measurement data 24d or what artifacts are generated in which measurement data 24d. As a result, doctors, laboratory technicians, etc., can discard certain measurement data 24d, enabling accurate diagnosis of the cerebral activity of the subject. Further, the scalp surface image 24a and the brain surface image 24b are created, and therefore, regardless of individual difference of the brain anatomical structure, the cerebral activity can be considered in detail.

Figure 4:
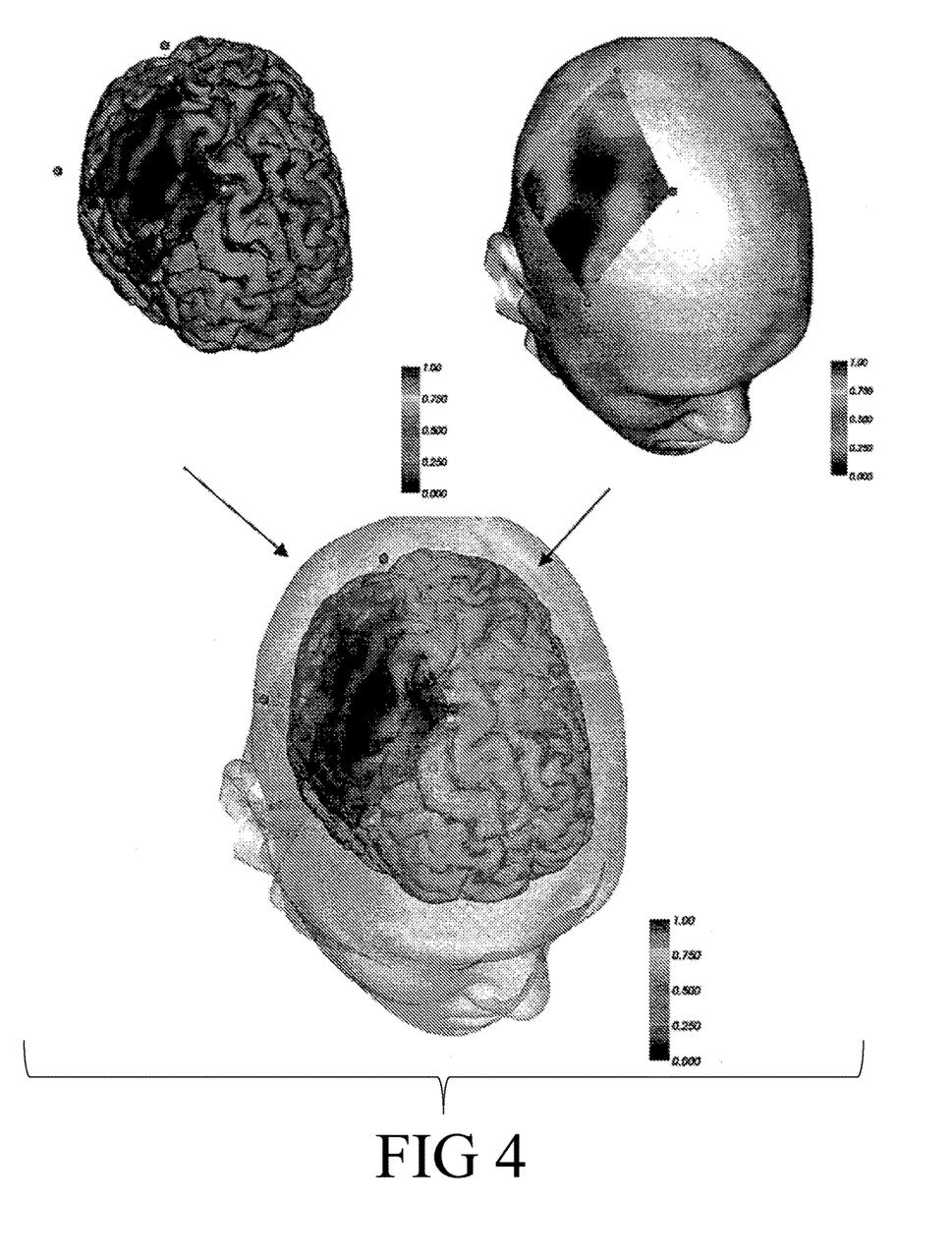
FIG. 4 is a view showing another example of the monitor screen displaying images obtained by the photobiological measurement apparatus.

OTHER EMBODIMENT (1) In the aforementioned photobiological measurement apparatus 1, a structure is exemplified, in which the data display controller 34 performs an image display of measurement data 24d on twenty-four (24) predetermined positions of the brain surface image 24b. However, it can be configured such that the counter line map of the measurement data 24d is displayed within a predetermined range of the brain surface image 24b. Further, a structure is exemplified in which the data display controller 34 performs an image display of the scalp blood flow data 24e of four (4) predetermined positions of the skin surface image 24a. Each of the four (4) predetermined positions may correspond to an area or location of the scalp located between one of the four light-receiving probes 14a-14d and a neighboring the light transmitting probe $12_{Tn}$ (e.g., the nearest light transmitting probe $12_{Tn}$ or one spaced by the first setting distance r1). It also may be configured to perform an image display of a contour line map of the skin blood flow data 24e within a predetermined range of the skin surface image 24a. FIG. 4 is a view showing another example of a monitor screen displaying images.

Figure 5:
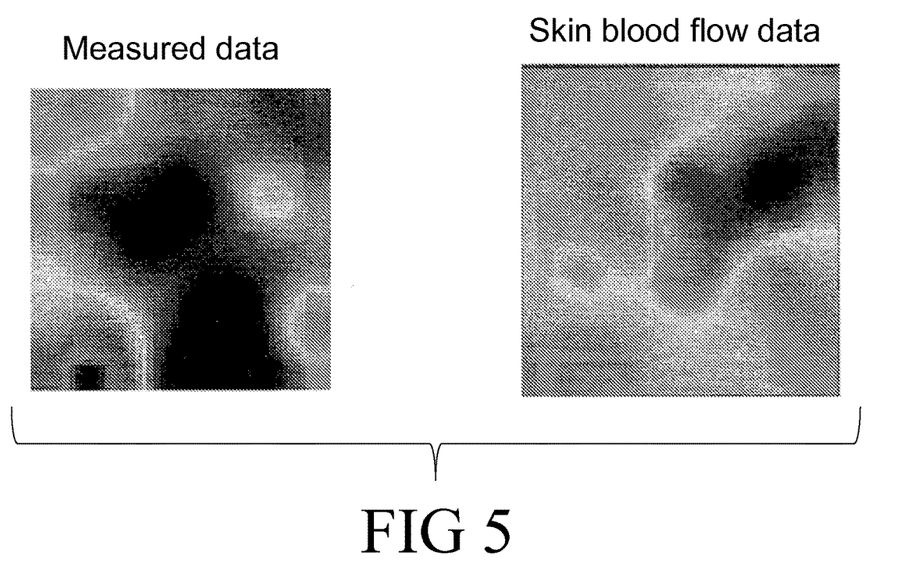
FIG. 5 is a view showing still another example of the monitor screen displaying images obtained by the photobiological measurement apparatus.

In the aforementioned photobiological measurement apparatus 1, a structure is exemplified, in which the data display controller 34 performs an image display of measurement data 24d on twenty-four (24) predetermined positions of the brain surface image 24b. However, it can be configured to perform an image display of the contour line map of the measurement data 24d without using the brain surface image 24b. Further, a structure is exemplified in which the data display controller 34 performs an image display of the scalp blood flow data 24e on four (4) predetermined positions of the skin surface image 24a. However, it can be configured to perform an image display of a contour line map of the skin blood flow data 24e without using the skin surface image 24a. FIG. 5 is a view showing another example of a monitor screen displaying images.

Figure 6:
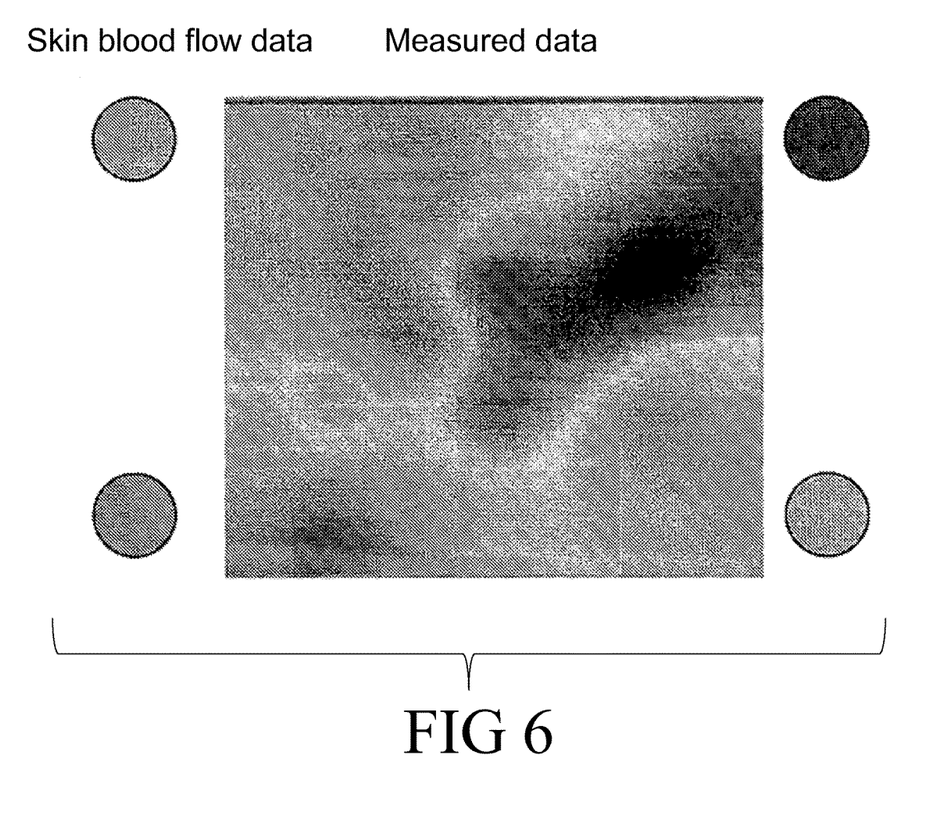
FIG. 6 is a view showing still yet another example of the monitor screen displaying images obtained by the photobiological measurement apparatus.

(3) In the aforementioned photobiological measurement apparatus 1, a structure is exemplified, in which the data display controller 34 performs an image display of skin blood flow data 24e on four (4) predetermined positions of the scalp surface image 24a. However, it can be configured to perform an image display of the skin blood flow data 24e near a predetermined position of the scalp of the subject with the contour line map of the measurement data 24d without using the scalp surface image 24a. FIG. 6 is a view showing still another example of a monitor screen displaying images.

The disclosed embodiments can be applied to a photobiological measurement apparatus for measuring cerebral activity in a noninvasive manner.

DESCRIPTION OF REFERENCE NUMERAL 1 photobiological measurement apparatus
12 light-transmitting probe
13 light-receiving probe
14 reference light-receiving probe
22 input device
23 display device
30 holder (light transmitting/receiving unit)
31 morphological image display acquisition unit
32 second received light quantity information calculation unit
33 first received light quantity information calculation unit
34 data display controller
50 MRI

The invention claimed is:

1. A photobiological measurement apparatus comprising:
a light-transmitting/receiving unit having a plurality of light-transmitting probes to be arranged on a scalp surface of a subject and a plurality of light-receiving probes to be arranged on the scalp surface, each of the light-receiving probes being arranged at a position away from the light-transmitting probe by a second setting distance r2;
a second received light quantity information calculation unit configured to calculate measurement data relating to cerebral activity using second received light quantity information ΔA2 from the light-transmitting probe to the light-receiving probe;
a data display controller configured to display measurement data in a predetermined range of a brain of the subject by respectively displaying the measurement data by indicating measurement positions of the brain of the subject;
a reference light-receiving probe arranged at a position away from the light-transmitting probe by a first setting distance r1 shorter than the second setting distance r2; and
a first received light quantity information calculation unit configured to calculate skin blood flow data relating to a skin blood flow using first received light quantity information ΔA1 from the light-transmitting probe to the reference light-receiving probe:
wherein the data display controller displays the measurement data in the predetermined range of the brain of the subject and the skin blood flow data while showing measurement positions of the scalp of the subject to display skin blood flow data at the predetermined position of the scalp of the subject.

2. The photobiological measurement apparatus as recited in claim 1, wherein the data display controller displays the measurement data in the predetermined range of the brain of the subject with a map, and also displays the skin blood flow data at a position near the predetermined position of the scalp of the subject in the map.

3. The photobiological measurement apparatus as recited in claim 1, further comprising a plurality of reference light-receiving probes,
wherein the data display controller displays the measured data in the predetermined range of the brain of the subject with a map, and also displays the skin blood flow data in the predetermined rang of the scalp of the object.

4. The photobiological measurement apparatus as recited in claim 2 or 3, further comprising a morphological image display controller configured to obtain and display a scalp surface morphological image a scalp surface of the subject and/or a brain surface morphological image showing a brain surface of the subject and display them,
wherein the map is displayed on a scalp surface morphological image and/or the brain surface morphological image in a superimposed manner.

* * * * *